Aug 7, 1951 E. S. BOERNER Plant Pat. 1,026
ROSE PLANT
Filed May 29, 1950
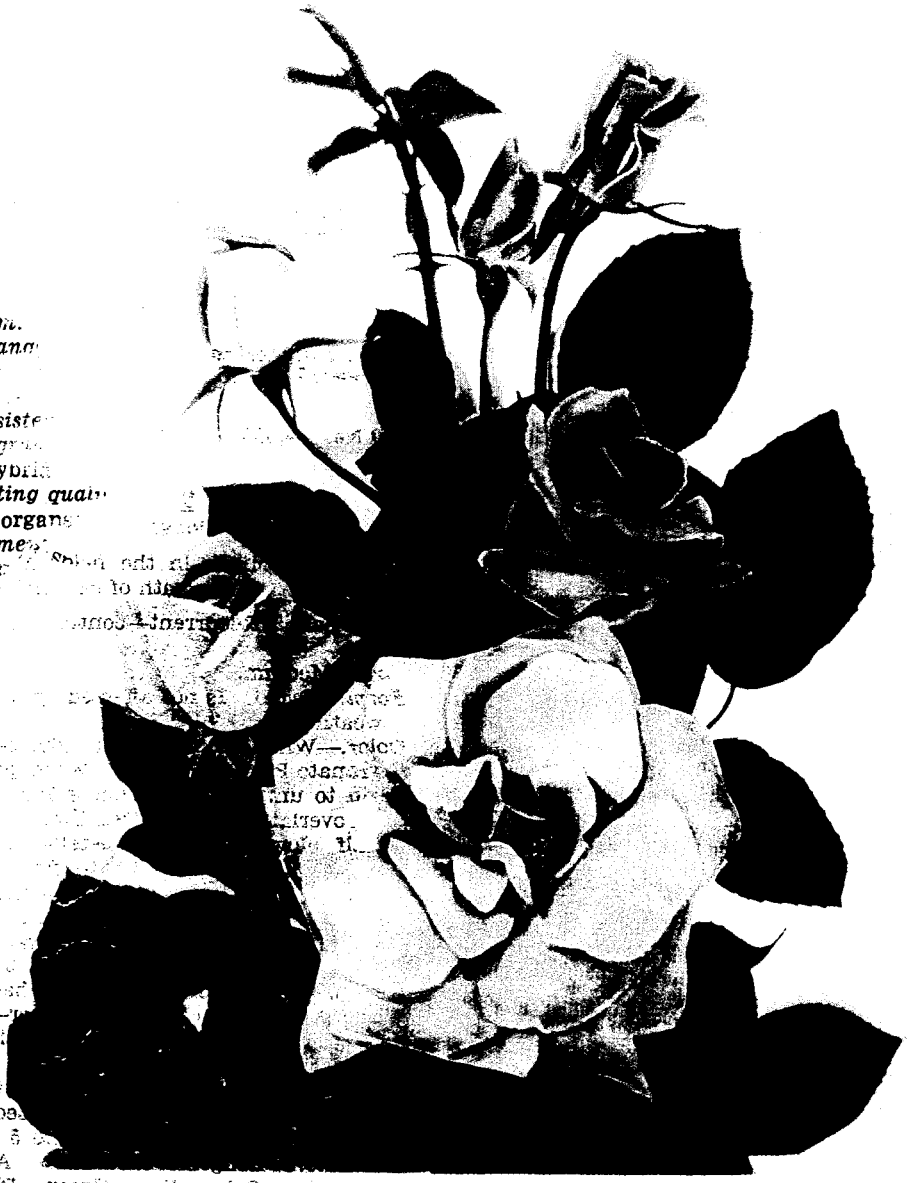
*Form.*
*Arrang*
*Persiste*
*Frag*
hybri
*Lasting qua*
Genital organs
*Stame*
E
Inventor.
E. S. Boerner
By: Robbins Robb
Attorneys.

BEST AVAILABLE COPY

Patented Aug. 7, 1951

Plant Pat. 1,026

UNITED STATES PATENT OFFICE 1,026

ROSE PLANT

Eugene S. Boerner, Newark, N. Y., assignor to Jackson & Perkins Company, Newark, N. Y., a corporation of New York Application May 29, 1950, Serial No. 164,898

1 Claim. (Cl. 47—61)

The present invention relates to a new and distinct variety of rose plant of the large-flowered polyantha class, originated by a cross of the variety of "Joanna Hill" (unpatented) × "World's Fair" (Plant Patent No. 362).

The parent variety "World's Fair" is a large-flowered polyantha rose and is primarily characterized by its vigorous habit of growth, producing strong shoots bearings flowers ranging in the colors Carmine and Oxblood red.

In originating the new variety of the present application, the principal objective was to obtain a lighter colored rose of the same type, while at the same time preserving the other important and desirable features of "World's Fair."

This objective was fully achieved in this new variety, as evidenced by the following combination of dominant characteristics which distinguish the new variety from its parents, as well as from other known varieties:

(1) The warm Eosine Pink color of the large-sized flowers which are borne in the floribunda habit of bloom;

(2) The large size and vigorous growth of the bush, producing strong stems as long as four feet or more; and (3) The constant repeating of flowers on the tips throughout the summer.

Asexual reproduction of this new variety by budding at Newark, New York, and at Pleasanton, California, shows that the foregoing characteristics come true to form and are established and transmitted through succeeding propagations.

The accompanying drawings shows specimens of the new variety, with the flowers in different stages of development from small bud to full-open bloom.

The following is a detailed description of the new variety, with color terminology in accordance with Ridgway's Color Standards and Nomenclature:

Parentage: Seedling.
*Seed parent.*—"Joanna Hill."
*Pollen parent.*—"World's Fair."
Classification:
*Botanic.*—Large flowered polyantha.
*Commercial.*—Floribunda Park Rose type.

*Flower*

(Observations made in [illegible] New York, late in the month [illegible]

Blooming habit: Recurrent—[illegible]
Bud:
*Size.*—Medium.
*Form.*—Ovoid. Is not affected by wet or weather.
*Color.*—When sepals first divide—Pomegranate Purple, Plate 12. When petals begin to unfurl—Pomegranate Purple, Plate 12, overlaid with Rose Red, Plate 12. When half blown—inside of petals—Rose Red, Plate 12, lightly overcast with Begonia Rose, Plate 1. Reverse of petals—Begonia Rose, Plate 1, lightly overcast with Rose Red, Plate 12. Lower half of the petal suffused with Light Orange Yellow, Plate 3.
*Sepals.*—Slightly branched. Curl b[illegible] petals begin to unfurl. Colo[illegible] Kildare Green, Plate 31; outside [illegible] Green, Plate 5.
*Calyx.*—Shape — apple. Size — sma[illegible] pect—smooth. Odor when rubb[illegible] none. Color—Oil Green, Plate [illegible]
*Peduncle.* — Length — medium. [illegible] smooth.
Strength [illegible]
*Opening.*—[illegible] fected by a[illegible]
Bloom:
*Size.*—Large [illegible] panded, [illegible]
*Borne.*—Se[illegible] irregular [illegible]
*Stems.*—Me[illegible]
*Form.*—Whe[illegible] manence—[illegible]
*Petalage.*—Dou[illegible] Number of p[illegible] 25.
*Color.*—Center [illegible] 1, overcast [illegible]
Outer p[illegible] lightly over[illegible]
Base of pet[illegible]
Inside of p[illegible]

BEST AVAILABLE COPY lightly overcast with La France Pink, Plate 1. Reverse of petals—La France Pink, Plate 1, lightly overcast with Rose Pink, Plate 12. Lower part of the petal suffused with Pale Orange Yellow, Plate 3. General tonality from a distance—Eosine Pink, Plate 1, overcast with La France Pink, Plate 1.

*Discoloration.*—General tonality at end of first day—Eosine Pink, Plate 1. Second day—Eosine Pink, Plate 1, overcast with La France Pink, Plate 1. Third day—La France Pink, Plate 1, overcast with Rose Pink, Plate 12.

Petals:

*Texture.*—Thin. Are not affected by wet or hot weather.

*Appearance.*—Inside — satiny. Outside — shiny.

—C l.

t.—Imbricated (regularly ar- hingle like). Petaloids in cen- nd large.

Drop off cleanly.

light. Nature — tea (average cent).

y.—On the plant—long.

thers — Large, many. Color — low, Plate 4. Arrangement— ular around styles.

*Stamens, filaments (threads).*—Long. Color—Picric Yellow, Plate 4.

*Pollen.*—Color — Pinard Yellow, Plate 4.

*Styles.*—Bunched, uneven length. Medium, thin.

*Stigmas.*—Color—Sulphur Yellow, Plate 5.

*Ovaries.*—All enclosed in calyx.

*Plant*

Form: Bush.

Growth: Vigorous, upright, stems growing 4 ft. or better.

Foliage: 3 to 5 leaflets.

*Size.*—Medium.

*Quantity.*—Normal.

*Color.*—New foliage — upper side — Spinach Green, Plate 5, lightly overcast with Oxblood Red, Plate 1; serrations—Oxblood Red, Plate 1; under side—Yellowish Oil Green, Plate 5, overcast with Oxblood Red, Plate 1. Old foliage—upper side—Dark Cress Green, Plate 31. Under side—Light Cress Green, Plate 31.

*Shape.*—Oval pointed.

*Texture.*— Upper side — leathery. Under side—smooth. Ribs and veins—ordinary.

*Edge.*—Serrated (saw toothed).

*Serration.*—Single, small.

*Leaf stem.*—Color—Courge Green, Plate 17. Under side—smooth.

*Stipules.*—Medium length, smooth.

*Disease resistance.*—Resistant.

Wood:

*New wood.*—Color—Yellowish Oil Green, Plate 5. Bark—smooth.

*Old wood.*—Color—Cedar Green, Plate 6. Bark—smooth.

Thorns:

*Thorns.*—Quantity—on main stalks from base and on laterals from stalk—ordinary. Form — narrow base, medium length, straight. Color when young — Carmine, Plate 1. Position—irregular.

*Prickles.*—Quantity—on main stalks and on laterals—none.

*Short Needles.*—Quantity—on main stalks and on laterals—none.

I claim:

A new and distinct variety of rose plant of the large flowered polyantha class, characterized as to novelty by the warm, Eosine Pink color of the large-sized flowers borne in the floribunda habit of bloom, by the large size and vigorous growth of the bush, by its long, strong stems, and by the constant repeating of flowers on the tips throughout the summer, substantially as shown and described.

EUGENE S. BOERNER.

No references cited.